United States Patent
Khanna et al.

(10) Patent No.: US 10,525,059 B2
(45) Date of Patent: *Jan. 7, 2020

(54) PHARMACEUTICAL COMPOSITIONS COMPRISING AFATINIB

(71) Applicant: FRESENIUS KABI ONCOLOGY LTD., New Delhi (IN)

(72) Inventors: Rajesh Khanna, Haryana (IN); Neeraj Kumar, Haryana (IN); Vijay Kumar Sharma, Haryana (IN); Ankit Gaur, Haryana (IN); Dhiraj Khattar, Haryana (IN)

(73) Assignee: Fresenius Kabi Oncology, Ltd., New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/753,525

(22) PCT Filed: Aug. 19, 2016

(86) PCT No.: PCT/IB2016/054969
§ 371 (c)(1),
(2) Date: Feb. 19, 2018

(87) PCT Pub. No.: WO2017/033107
PCT Pub. Date: Mar. 2, 2017

(65) Prior Publication Data
US 2018/0235967 A1    Aug. 23, 2018

(30) Foreign Application Priority Data

Aug. 21, 2015  (IN) ............................ 2604/DEL/2015

(51) Int. Cl.
| *A61K 9/20* | (2006.01) |
| *A61K 31/517* | (2006.01) |
| *A61P 35/00* | (2006.01) |

(52) U.S. Cl.
CPC .......... *A61K 31/517* (2013.01); *A61K 9/2009* (2013.01); *A61K 9/2018* (2013.01); *A61K 9/2027* (2013.01); *A61K 9/2054* (2013.01); *A61K 9/2095* (2013.01); *A61P 35/00* (2018.01)

(58) Field of Classification Search
None
See application file for complete search history.

(56) References Cited

U.S. PATENT DOCUMENTS

| RE43,431 E | 5/2012 | Himmelsbach et al. |
| 8,426,586 B2 | 4/2013 | Soyka et al. |
| 8,545,884 B2 * | 10/2013 | Messerschmid ...... A61K 9/0095 |
| | | 424/465 |
| 2005/0085495 A1 | 4/2005 | Soyka et al. |
| 2009/0318480 A1 | 12/2009 | Solca |
| 2014/0051713 A1 * | 2/2014 | Gidwani .............. C07D 405/12 |
| | | 514/266.24 |
| 2017/0240533 A1 | 8/2017 | Singh et al. |

FOREIGN PATENT DOCUMENTS

| CN | 104 744 445 A | 7/2015 |
| EP | 3 023 421 A1 | 5/2016 |
| IN | 1769/DEL/2015 A | 12/2016 |
| WO | WO 2012/121764 A1 | 9/2012 |
| WO | WO 2013/052157 A1 | 4/2013 |
| WO | WO 2013052157 * | 4/2013 |
| WO | WO 2016/027243 A1 | 2/2016 |
| WO | WO 2016/051380 A1 | 4/2016 |

OTHER PUBLICATIONS

Wu et al. "Insensitivity of Compaction Properties of Brittle Granules to Size Enlargement by Roller Compaction" 2007.*
European Patent Office, International Search Report in International Application No. PCT/IB2016/054969 (dated Nov. 10, 2016).
European Patent Office, Written Opinion in International Application No. PCT/IB2016/054969 (dated Nov. 10, 2016).
International Bureau of WIPO, International Preliminary Report on Patentability in International Application No. PCT/IB2016/054969 (dated Feb. 27, 2018).
Caira, "Crystalline Polymorphism of Organic Compounds," *Topics in Current Chemistry*, vol. 198, pp. 163-208, Springer, Berlin, Germany (1998).
European Patent Office, Communication Pursuant to Rule 164(2)(b) and Article 94(3) EPC (dated Apr. 23, 2019).

* cited by examiner

*Primary Examiner* — Robert A Wax
*Assistant Examiner* — Danah Al-Awadi
(74) *Attorney, Agent, or Firm* — Leydig, Voit & Mayer, Ltd.

(57) ABSTRACT

The present invention relates to a tablet comprising Afatinib or a pharmaceutically acceptable salt thereof, wherein the tablet is obtained by direct compression. The present invention further relates to a process for manufacturing a tablet of the invention as well as the use of the tablet of the invention.

20 Claims, 1 Drawing Sheet

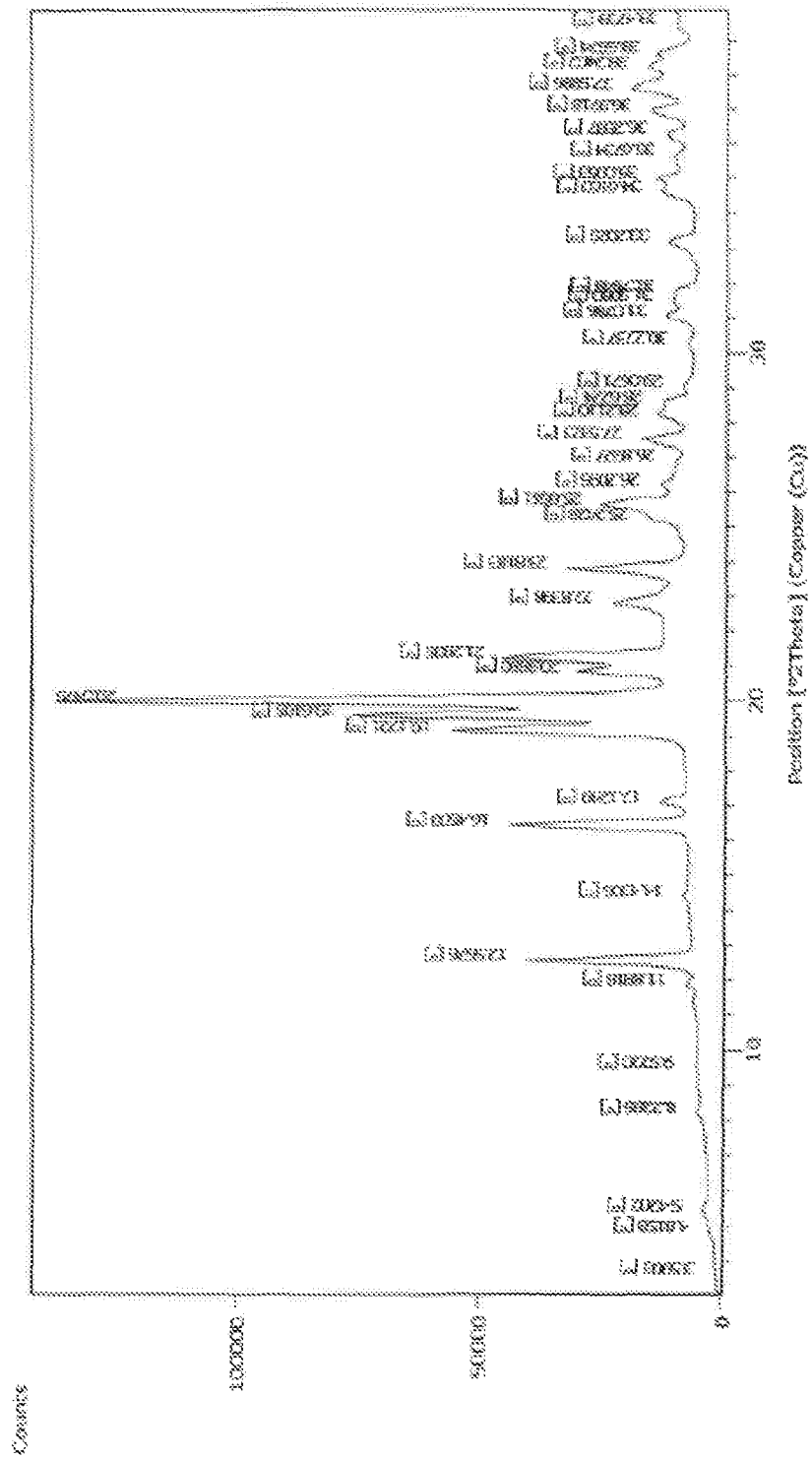

PHARMACEUTICAL COMPOSITIONS COMPRISING AFATINIB

CROSS-REFERENCE TO RELATED APPLICATIONS

This patent application is the U.S. national phase of International Application No. PCT/IB2016/054969, filed on Aug. 19, 2016, which claims the benefit of Indian Patent Application No. 2604/DEL/2015, filed Aug. 21, 2015, the disclosures of which are incorporated herein by reference in their entireties for all purposes.

FIELD OF THE INVENTION

The present invention relates to pharmaceutical compositions comprising Afatinib or a pharmaceutically acceptable salt thereof. The present invention further relates to a process for manufacturing the compositions as well as the use of the compositions of the invention.

BACKGROUND OF THE INVENTION

Afatinib is a 4-anilinoquinazoline compound, chemically known as 4-[(3-chloro-4-fluorophenyl)amino]-6-{[4-(N,N-dimethylamino)-1-oxo-2 buten-1yl]amino}-7-((s)-tetrahydrofuran-3-yloxy) quinazoline:

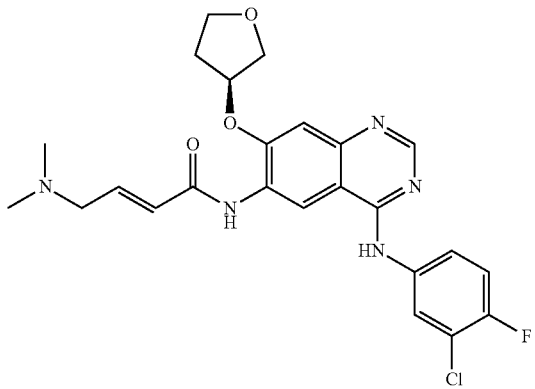 [SMILES: CN(C)C/C=C/C(=O)Nc1cc2c(Nc3ccc(F)c(Cl)c3)ncnc2cc1O[C@H]1CCOC1]

Afatinib is a tyrosine kinase inhibitor which covalently binds to the kinase domains of EGFR (ErbB1), HER2 (ErbB2), and HER4 (ErbB4) and irreversibly inhibits tyrosine kinase autophosphorylation, resulting in downregulation of ErbB signalling.

Afatinib is approved as its dimaleate salt and is sold under the brand name Gilotrif® in the United States of America and Giotrif® in European countries by Boehringer Ingelheim. It is currently marketed in form of film coated tablets comprising 20, 30, 40 mg and 50 mg (in European countries) Afatinib for oral administration. Afatinib is indicated for the first-line treatment of metastatic non-small cell lung cancer (NSCLC).

The substance Afatinib is disclosed in U.S. RE43,431.

A process for the preparation of Afatinib dimaleate is described in U.S. Pat. No. 8,426,586. The process yields a crystalline polymorph, herein further referred to as "form A". In U.S. Pat. No. 8,426,586 form A of Afatinib dimaleate is characterized by X-ray powder diffraction (XRPD) and differential scanning calorimetry (DSC).

According to U.S. Pat. No. 8,426,586 Afatinib dimaleate only exists in one crystalline modification i.e. form A. However, in the meantime further crystalline polymorphs of Afatinib dimaleate have been discovered.

For example crystalline Afatinib dimaleate form C, form D and form E are described in WO 2013/052157.

WO2012/121764 discloses crystalline form B of Afatinib dimaleate and form A, form B, form C and form D of Afatinib free base. Also, some other crystalline salt forms of Afatinib including difumarate, dioxalate, dimesylate, disulfate, di hydrochloride, di succinate salt forms along with some amorphous forms including Afatinib di-L-malate and Afatinib citrate are described.

U.S. Pat. No. 8,545,884 discloses a tablet comprising Afatinib dimaleate prepared by dry granulation via roller compaction. It teaches that an intermediate compaction step is crucial for the tabletting of Afatinib. This process is tedious and requires specific equipment (roller compactor). Also the yield is lower. Thus, there is a need for a more convenient manufacturing process suitable for large scale production which is cost effective and minimises the losses during manufacturing at the same time providing tablets of adequate hardness, proper disintregation time, appropriate dissolution profiles and good storage stability.

SUMMARY OF THE INVENTION

It has now surprisingly been found that Afatinib may be tabletted by direct compression, thus overcoming the above-mentioned difficulties and drawbacks. The invention provides a simple, easy, single step, cost effective, direct tableting manufacturing process.

Thus the present invention relates to a tablet comprising Afatinib or a pharmaceutically acceptable salt thereof, wherein the tablet is obtained by direct compression.

The present invention further relates to a tablet for oral administration comprising crystalline Afatinib dimaleate form A, form F, form G, form H, form I, form J, form K, form L or form M, wherein the tablet is obtained by direct compression.

The present invention also relates to a tablet for oral administration comprising crystalline Afatinib form E or form F, wherein the tablet is obtained by direct compression.

The present invention further relates to a process for manufacturing a tablet of the invention as well as the use of the tablet of the invention.

Particularly preferred embodiments are set forth in the claims.

DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

Abbreviations

XRPD: X-ray powder diffraction
DSC: Differential scanning calorimetry
TGA: Thermal gravimetric analysis
RSD: Relative Standard Deviation

BRIEF DESCRIPTION OF THE DRAWING

The FIGURE shows the XRPD of tablet with crystalline Afatinib dimaleate polymorphic form L.

TABLET

The term "tablet" as mentioned herein refers to a solid dosage form usually obtained by compression of an active pharmaceutical ingredient, preferably in admixture with one or more pharmaceutically acceptable excipients using a tableting machine. A tablet may be uncoated or coated.

The compositions according to the present invention are tablets comprising Afatinib or a pharmaceutically acceptable salt thereof and preferably one or more pharmaceutically acceptable excipients.

Tablets for oral administration have to be comparable with the innovator product) (Gilotrif® in terms of dissolution profile, hardness, content uniformity, disintegration time and storage stability.

Preferably, the tablet according to present invention comprises crystalline Afatinib or a pharmaceutically acceptable salt thereof.

More preferably, the tablet according to present invention comprises crystalline Afatinib dimaleate.

Preferably, the tablet according to present invention comprises crystalline Afatinib dimaleate form A, form F, form G, form H, form I, form J, form K, form L, form M or crystalline Afatinib form E or form F.

"Active Pharmaceutical Ingredient"

The term "Active Pharmaceutical Ingredient" (API) as mentioned herein refers to Afatinib or to a pharmaceutically acceptable salt thereof.

Afatinib or a Pharmaceutically Acceptable Salt Thereof

As used herein, the expression "Afatinib" refers to Afatinib free base prepared according to methods known in art, e.g. as described in U.S. RE43,431 and U.S. Pat. No. 8,426,586 and also in our co-pending application IN 1769/DEL/2015 filed on Jun. 12, 2015.

The term "Afatinib or a pharmaceutically acceptable salt thereof" as mentioned herein refers to Afatinib free base and to all available pharmaceutically acceptable salts of Afatinib.

Afatinib or a pharmaceutically acceptable salt thereof comprises Afatinib free base and various salt forms which including dimaleate, difumarate, dioxalate, dimesylate, disulfate, dihydrochloride, disuccinate, di-L-malate and citrate salt. Afatinib free base and Afatinib dimaleate salt are especially preferred.

Afatinib or a pharmaceutically acceptable salt thereof may exist in various polymorphic forms.

Crystalline Afatinib form E and F and crystalline Afatinib dimaleate form F, form G, form H, form I, form J, form K, form L and form M as described in our co-pending application IN 1769/DEL/2015 filed on Jun. 12, 2015 are preferred. Crystalline Afatinib dimaleate form L is particularly preferred.

The crystalline forms E and F of Afatinib and forms F to M of Afatinib dimaleate are characterized by X-ray powder diffraction (XRPD), differential scanning calorimetry (DSC) and thermogravimetric analysis (TGA).

Crystalline form E of Afatinib is characterized by at least one of:
a) an X-ray powder diffractogram having peaks at 5.2, 10.4, 12.4, 14.4±0.2 degrees two-theta;
b) an endothermic peak at 91±2° C. as measured by differential scanning calorimetry (DSC); and
c) a weight loss of about 2.3±1% as measured by thermogravimetric analysis (TGA).

Crystalline form E of Afatinib can be further characterized by its X-ray powder diffractogram having peaks at 5.2, 10.4, 12.4, 13.2, 14.4, 17.8, 18.5, 21.0, 22.5, 23.6 and 27.4±0.2 degrees two-theta.

Crystalline form F of Afatinib is characterized by at least one of:
a) an X-ray powder diffractogram having peaks at 6.1, 12.2, 13.4, 16.3, 18.8, 20.5 and 24.6±0.2 degrees two-theta;
b) an endothermic peak at 102±2° C. as measured by differential scanning calorimetry (DSC); and
c) by a weight loss of about 3.6±1% as measured by thermogravimetric analysis (TGA).

Crystalline form F of Afatinib of the present invention can be further characterized by its X-ray powder diffractogram having peaks at 5.2, 5.5, 6.1, 8.2, 10.9, 12.2, 12.5, 13.4, 16.3, 16.7, 17.5, 18.8, 19.2, 20.5, 21.1, 21.4, 21.7, 22.1, 22.5, 22.9, 23.6, 24.1, 24.6, 25.2, 25.7, 26.8, 26.9, 27.4, 28.0, 28.7, 29.7, 30.0, 30.5, 31.3, 32.3, 32.7, 33.6, 34.4, 35.6, 37.6, 38.1 and 38.6±0.2 degrees two-theta.

Crystalline form F of Afatinib dimaleate is characterized by at least one of:
a) an X-ray powder diffractogram having peaks at 5.1, 11.0, 17.9, 20.2, 20.8 and 25.7±0.2 degrees two-theta;
b) an endothermic peak at 115±2° C. as measured by differential scanning calorimetry (DSC); and
c) a weight loss of about 2.6±1%, as measured by thermogravimetric analysis (TGA).

Crystalline form F of Afatinib dimaleate can be further characterized by an X-ray powder diffractogram having peaks at 3.7, 5.1, 5.5, 6.6, 9.0, 10.1, 11.0, 12.5, 13.6, 15.4, 16.4, 17.9, 20.2, 20.8, 21.6, 22.9, 25.7, 26.8 and 33.3±0.2 degrees two-theta.

Crystalline form G of Afatinib dimaleate is characterized by at least one of:
a) an X-ray powder diffractogram having peaks at 5.1, 9.7, 10.7, 21.6, 25.7±0.2 degrees two-theta;
b) an endothermic peak at 152±2° C. as measured by differential scanning calorimetry (DSC); and
c) by a weight loss of about 0.4±1% as measured by thermogravimetric analysis (TGA).

Crystalline form G of Afatinib dimaleate of the present invention can be further characterized by its X-ray powder diffractogram having peaks 5.1, 9.7, 10.7, 14.3, 15.0, 16.0, 16.5, 16.9, 17.8, 17.9, 18.4, 18.8, 19.4, 20.3, 20.9, 21.6, 22.9, 23.9, 24.8, 25.7, 26.9, 28.7 and 36.6±0.2 degrees two-theta.

Crystalline form H of Afatinib dimaleate is characterized by at least one of:
a) an X-ray powder diffractogram having peaks at 5.4, 6.5, 10.2, 12.7, 17.7, 21.7, and 25.3±0.2 degrees two-theta;
b) an endothermic peak at 118±2° C. as measured by differential scanning calorimetry (DSC); and
c) by a weight loss of about 0.6±1% as measured by thermogravimetric analysis (TGA).

Crystalline form H of Afatinib dimaleate can be further characterized by its X-ray powder diffractogram having peaks at 5.4, 6.5, 7.1, 10.2, 11.4, 12.0, 12.7, 13.2, 13.6, 16.1, 17.2, 17.7, 19.7, 20.3, 21.7, 22.9, 23.9, 25.3, 26.4, 27.9, 31.3, 33.0 and 36.1±0.2 degrees two-theta.

Crystalline form I of Afatinib dimaleate is characterized by at least one of:
a) an X-ray powder diffractogram having peaks at 5.5, 6.2, 11.3, 22.2 and 25.1±0.2 degrees two-theta;
b) endothermic peaks at 114 and 169±2° C. as measured by differential scanning calorimetry (DSC); and
c) a weight loss of about 4.2±1% as measured by thermogravimetric analysis (TGA).

Crystalline form I of Afatinib dimaleate can be further characterized by its X-ray powder diffractogram having peaks at 3.9, 5.3, 5.5, 5.6, 6.2, 8.8, 10.0, 11.0, 11.3, 12.4, 15.0, 16.0, 17.6, 18.8, 22.2 and 25.1±0.2 degrees two-theta Crystalline form J of Afatinib dimaleateis characterized by at least one of:
a) an X-ray powder diffractogram having peaks at 4.9, 10.9, 18.3, 20.3, 25.3 and 26.1, ±0.2 degrees two-theta;
b) endothermic peaks at 123, 136 and 158±2° C. as measured by differential scanning calorimetry (DSC); and
c) by a weight loss of about 1.9±1% as measured by thermogravimetric analysis (TGA).

Crystalline form J of Afatinib dimaleate can be further characterized by its X-ray powder diffractogram having peaks at 4.0, 4.9, 5.5, 6.9, 8.0, 9.0, 10.9, 12.4, 13.6, 13.9, 14.5, 16.2, 16.7, 17.4, 17.8, 18.3, 18.8, 19.2, 20.3, 21.3, 21.6, 23.0, 24.8, 25.3, 26.1, 27.2, 28, 29.2, 29.9, 31.2, 32.7, 33.7 and 35.8±0.2 degrees two-theta.

Crystalline form K of Afatinib dimaleateis characterized by at least one of:
a) an X-ray powder diffractogram having peaks at 4.9, 5.4, 22.3, and 25.2±0.2 degrees two-theta;
b) endothermic peaks at 105, 129 and 166±2° C. as measured by differential scanning calorimetry (DSC); and
c) by a weight loss of about 0.8±1% as measured by thermogravimetric analysis (TGA).

Crystalline form K of Afatinib dimaleate can be further characterized by its X-ray powder diffractogram having peaks at 4.9, 5.4, 11.0, 12.7, 20.3, 22.3 and 25.2±0.2 degrees two-theta.

Crystalline form L of Afatinib dimaleateis characterized by at least one of:
a) an X-ray powder diffractogram having peaks at 5.2, 10.3, 11.1, 15.5, 18.1±0.2 degrees two-theta;
b) endothermic peaks at 125 and 171±2° C. as measured by differential scanning calorimetry (DSC); and
c) a weight loss of about 2.0±1% as measured by thermogravimetric analysis (TGA).

Crystalline form L of Afatinib dimaleate of the present invention can be further characterized by its X-ray powder diffractogram having peaks at 4.2, 5.2, 7.0, 8.5, 10.3, 11.1, 12.2, 12.7, 13.4, 15.5, 16.6, 18.1, 18.4, 20.4, 21.2, 23.0, 24.4, 24.9, 25.7, 26.7, 28.4, 29.7, 33.4 and 35.9±0.2 degrees two-theta.

Crystalline form M of Afatinib dimaleateis characterized by at least one of:
a) an X-ray powder diffractogram having peaks at 5.0, 5.4, 17.3, 19.9 and 25.5±0.2 degrees two-theta;
b) endothermic peaks at 112 and 172±2° C. as measured by differential scanning calorimetry (DSC); and
c) a weight loss of about 2.1±1% as measured by thermogravimetric analysis (TGA).

Crystalline form M of Afatinib dimaleate can be further characterized by its X-ray powder diffractogram having peaks at 5.0, 5.4, 6.6, 7.4, 8.1, 8.6, 10.5, 11.4, 12.9, 13.2, 13.7, 14.9, 16.2, 16.9, 17.3, 19.9, 21.0, 22.5, 23.4, 24.5, 25.5, 26.1, 26.9, 28.0, 29.1, 32.8 and 37.7±0.2 degrees two-theta.

The polymorphs described in our co-pending application 1769/DEL/2015 filed on Jun. 12, 2015 are prepared using following process:

The process for the preparation of crystalline form E of Afatinib, comprising:
a) dissolving Afatinib in acetone;
b) adding methyl tertiary butyl ether; and
c) isolating crystalline form E of Afatinib.

The process for the preparation of crystalline form F of Afatinib, comprising,
a) dissolving Afatinib in dichloromethane;
b) adding methyl tertiary butyl ether; and
c) isolating crystalline form F of Afatinib.

The process for the preparation of crystalline form F of Afatinib dimaleate, comprising:
a) dissolving Afatinib in ethyl acetate;
b) adding maleic acid; and
c) isolating crystalline form F of Afatinib dimaleate.

The process for the preparation of crystalline form G of Afatinib dimaleate, comprising:
a) dissolving Afatinib in dimethyl formamide;
b) adding maleic acid;
c) adding methyl tertiary butyl ether; and
d) isolating crystalline form G of Afatinib dimaleate.

The process for the preparation of crystalline form H of Afatinib dimaleate, comprising:
a) dissolving Afatinib in acetonitrile;
b) adding maleic acid; and
c) isolating crystalline form H of Afatinib dimaleate.

The process for the preparation of crystalline form I of Afatinib dimaleate, comprising:
a) dissolving Afatinib in dimethyl formamide;
b) adding maleic acid;
c) adding dichloromethane; and
d) isolating crystalline form I of Afatinib dimaleate.

The process for the preparation of crystalline form J of Afatinib dimaleate, comprising:
a) dissolving Afatinib in acetone;
b) adding methyl tertiary butyl ether;
c) adding maleic acid; and
d) isolating crystalline form J of Afatinib dimaleate.

The process for the preparation of crystalline form K of Afatinib dimaleate, comprising,
a) dissolving Afatinib in ethyl acetate;
b) adding methyl tertiary butyl ether;
c) adding maleic acid; and
d) isolating crystalline form K of Afatinib dimaleate.

The process for the preparation of crystalline form L of Afatinib dimaleate, comprising:
a) dissolving Afatinib in acetonitrile;
b) adding maleic acid;
c) isolating form H of Afatinib dimaleate;
d) treating with ethyl acetate; and
e) isolating crystalline form L of Afatinib dimaleate.

The process for preparation of crystalline form L of Afatinib dimaleate comprising:
a) treating the crystalline form H of Afatinib dimaleate with ethyl acetate; and
b) isolating crystalline form L of Afatinib dimaleate.

The process for preparation of crystalline form L of Afatinib dimaleate comprising:
a) reacting a compound of formula II

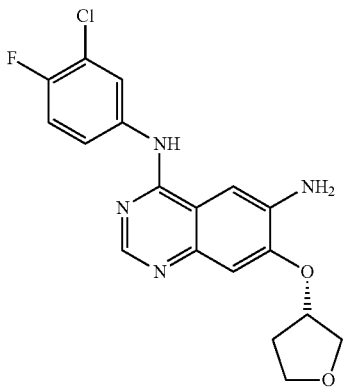

Formula II with a compound of formula III, or a salt thereof

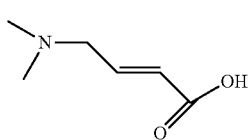

Formula III to obtain Afatinib of formula I,

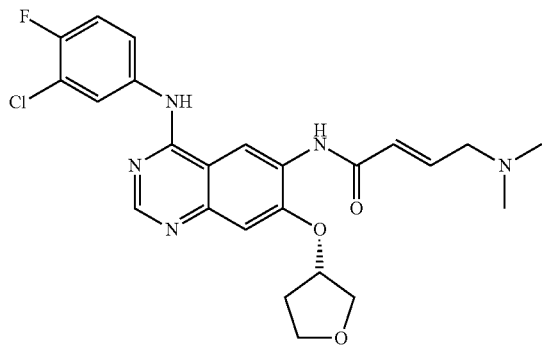

Formula I in the presence of a suitable solvent and dehydrating reagent, at a temperature between −40 to 0° C.; and
b) converting the compound of formula I into the crystalline form L of Afatinib dimaleate.

The process for the preparation of crystalline form M of Afatinib dimaleate, comprising:
a) dissolving Afatinib in acetonitrile;
b) adding solution of maleic acid in dimethyl sulfoxide and acetonitrile;
c) treating with ethyl acetate; and
d) isolating crystalline form M of Afatinib dimaleate.

Afatinib or a pharmaceutically acceptable salt thereof also may exist in other polymorphic forms such as form A, form B, form C and form D as known in the prior art.

The active pharmaceutical ingredient may be present in the pharmaceutical composition in an amount of 1 to 50 wt. % based on total weight of tablet, preferably 5 to 40 wt. % based on total weight of tablet, more preferably 5 to 25 wt. %, most preferably 10 to 20 wt. % based on total weight of tablet.

The preferable particle size of Afatinib dimaleate is such that a $D_{90}$ from 30 to 70 μm, a $D_{50}$ from 5 to 30, a $D_{10}$ from 1 to 20 μm is warranted.

"The Pharmaceutically Acceptable Excipients"

The term "pharmaceutically acceptable excipients" as mentioned herein refers to components comprised in the tablet other than the API. They must be edible and pharmaceutically acceptable. The pharmaceutically acceptable excipients preferably comprise at least one filler, binder, disintegrant, lubricant and glidant.

Suitable fillers include e.g. sugars (e.g. monosaccharides such as glucose; oligosaccharides such as sucrose, disaccharides, such as lactose which may exist in various forms and in various crystalline modifications, including spray-dried, sieved, milled, granulated, anhydrous, micronized, precipitated, drum-dried, coprocessed with further excipients such as microcrystalline cellulose), sugar alcohols (e.g. sorbitol, mannitol, xylitol, lactitol, erythritol, dulcitol, ribitol and erythritol), cellulose, cellulose derivates (e.g. powdered cellulose, microcrystalline cellulose), starch, modified starch (e.g. pre-gelatinized, partially hydrolysed), solid inorganic substances (e.g. calcium phosphate, dibasic calcium phosphate, hydroxyl apatite, calcium sulphate, calcium carbonate), semisolid substances (e.g. lipids, paraffin) and mixtures thereof.

Preferably, the filler is selected from the group consisting of lactose, mannitol, microcrystalline cellulose, pregelatinized starch, calcium phosphate and dibasic calcium phosphate.

More preferably, the tablets comprise lactose monohydrate as a filler e.g. in spray dried, granulated or precipitated form. Lactose monohydrate may have a $D_{90}$ of 100 to 600 μm, preferably of 150 to 500 μm.

The filler is preferably present in an amount of 20 to 90 wt. % based on total weight of tablet, more preferably of 30 to 80 wt. % based on total weight of tablet and most preferably of 50 to 80 wt. % based on total weight of tablet.

Suitable binders include e.g cellulose, cellulose derivatives (e.g. microcrystalline cellulose, ethylcellulose, carboxymethylcellulose, hydroxypropyl methylcellulose, hydroxyethyl cellulose), starch, modified starch (e.g. pre-gelatinized, partially hydrolysed), polyethyleneglycol, polyvinylpyrrolidone, polyvinylacetate, polyvinyl alcohol co-polymerisates (e.g. Copovidone) and mixtures thereof.

Preferably, the binder is selected from the group consisting of microcrystalline cellulose, hydroxypropyl methyl cellulose, pregelatinized starch and polyvinylpyrrolidone. More preferably the binder is microcrystalline cellulose.

The binder is preferably present in an amount of 1 to 40 wt. % based on total weight of tablet, more preferably of 2 to 30 wt. % based on total weight of tablet and most preferably of 3 to 20 wt. % based on total weight of tablet.

Suitable disintegrants include e.g. low-substituted hydroxypropyl cellulose (HPC), sodium starch glycolate, crospovidone, croscarmellose, sodium carboxymethylcellulose, dried corn starch and mixtures thereof.

Preferably, the disintegrant is crospovidone.

The disintegrant is preferably present in an amount of 0.5 to 15 wt. % based on total weight of tablet, more preferably of 0.5 to 8 wt. % based on total weight of tablet and most preferably of 0.5 to 5 wt. % based on total weight of tablet.

Suitable glidants include e.g. colloidal silicon dioxide, light anhydrous silicic acid, crystalline cellulose and mixtures thereof.

Preferably, the glidant is colloidal silicon dioxide.

The glidant is preferably present in an amount of 0.1 to 5 wt. % based on total weight of tablet more preferably of 0.1 to 3 wt. % based on total weight of tablet and most preferably of 0.1 to 1.5 wt. % based on total weight of tablet.

Suitable lubricants include e.g. stearic acid, magnesium stearate, sodium stearylfumarate, glycerol tribehenate, polyethylene glycol and mixtures thereof.

Preferably, the lubricant is magnesium stearate.

The lubricant is preferably present in an amount of 0.5 to 10 wt. % based on total weight of tablet, more preferably of 0.5 to 8 wt. % based on total weight of tablet and most preferably of 0.5 to 5 wt. % based on total weight of tablet.

Apart from the above described excipients, the tablets according to the present invention may contain multi purpose excipients which possess both high binding characteristics and high fluidity which makes them apt for direct compression.

Suitable multipurpose excipients include modified excipients e.g. partially pregelatinisedstarch (PPG starch) and coprocessed excipients e.g. silicified microcrystalline cellulose (SMCC), coprocessed combination of cellulose and lactose, microcrystalline cellulose and guar gum, calcium carbonate and sorbitol, sucrose 3% dextrin.

These excipients are present in an amount depending on the function of the excipient in the tablet, preferably in range of 10 to 90 wt. % based on total weight of tablet.

The tablets according to the present invention may optionally be coated. Film coating may be present in the range of 2 to 5 wt. % based on the core tablet weight.

Suitable coating agents include e.g. film forming polymers and one or more additional excipients.

The film forming polymers may be dissolved in aqueous or non aqueous media.

Suitable film forming polymers include e.g. polyvinyl alcohol, polyvinyl pyrrolidone, hydroxypropyl cellulose, hydroxypropyl methyl cellulose, sodium carboxymethyl cellulose and mixtures thereof.

A hydroxypropyl methyl cellulose (HPMC) based coating is especially preferred.

The film forming polymer is preferably present in an amount of 40 to 90 wt. % based on total weight of film coating and more preferably in an amount of 50 to 80 wt. % based on total weight of the film coating.

The one or more additional excipients include e.g. plasticizers, colorants, dispersion aids, opacifiers and mixtures thereof.

Suitable plasticizers include e.g. glycerol, acetylated monoglycerides, citrate esters (e.g. triethyl citrate), propylene glycol, polyethylene glycols (e.g. polyethylene glycols with a molecular weight of from 200 to 500), polysorbates (e.g. polysorbate 80), triglycerides (e.g. castor oil, glycerol tri-acetat) or phthalate esters (e.g. diethyl phthalate).

The plasticizer is preferably present in an amount of 5 to 15 wt. % based on total weight of film coating and more preferably in an amount of 7 to 10 wt. % based on total weight of film coating Suitable opacifiers and colorants include e.g. titanium dioxide and ferric oxides (e.g. iron oxide red and yellow).

The opacifier is preferably present in an amount of 1 to 30 wt. % based on total weight of film coating and more preferably in an amount of 10 to 25 wt. % based on total weight of film coating.

The colorant is preferably present in an amount of 0.1 to 1.5 wt. % based on total weight of film coating and more preferably in an amount of 0.4 to 1 wt. % based on total weight of film coating.

Suitable dispersion aids include e.g. talcum.

The dispersion aid is preferably present in an amount of 1 to 10 wt. % based on total weight of film coating and more preferably in an amount of 2.5 to 7.5 wt. % based on total weight of film coating.

Preparation of the Tablet

The present invention further relates to the manufacturing of tablets for oral administration by direct compression.

The term "direct compression" as used herein refers to the compression of tablets without any preceding granulation step using a tabletting machine.

The tablets according to the present invention are prepared by the following process:

i) Providing Afatinib or a pharmaceutically acceptable salt thereof or a blend of Afatinib or a pharmaceutically acceptable salt thereof and one or more pharmaceutically acceptable excipients;

ii) Mixing Afatinib or a pharmaceutically acceptable salt thereof or the blend provided in step i) with at least one lubricant and iii) Compressing the lubricated blend provided in step ii) to form a tablet;

iv) Optionally coating the tablets obtained in step iii) with suitable film coating;

v) Packing the tablets obtained in step iii) or iv) in a suitable packaging material.

Use of the Tablet

The tablets according to the present invention are used for treating cancer in a subject in need thereof.

More specifically, the tablets according to the present invention are used for the treatment of Epidermal Growth Factor Receptor (EGFR) TKI-naïve adult patients with locally advanced or metastatic non-small cell lung cancer (NSCLC) with activating EGFR mutation(s).

The present invention includes inter alia the following aspects:

In a first aspect, the present invention relates to a tablet comprising Afatinib or a pharmaceutically acceptable salt thereof, wherein the tablet is obtained by direct compression.

In a second aspect, the present invention relates to a tablet according to aspect 1 comprising Afatinib dimaleate.

In a third aspect, the present invention relates to a tablet according to aspect 1 or 2 comprising crystalline Afatinib dimaleate.

In a fourth aspect, the present invention relates to a tablet according to any of the preceding aspects comprising crystalline Afatinib dimaleate form A, form F, form G, form H, form I, form J, form K, form L or form M, preferably form L.

In a fifth aspect, the present invention relates to a tablet according to aspect 1 comprising crystalline Afatinib, preferably crystalline Afatinib form E or form F.

In a sixth aspect, the present invention relates to a tablet according to any of the preceding aspects, further comprising one or more pharmaceutically acceptable excipients.

In a seventh aspect, the present invention relates to a tablet according to any of the preceding aspects comprising at least one filler, at least one binder, at least one disintegrant, at least one glidant and at least one lubricant.

In an eighth aspect, the present invention relates to a tablet according to any of the preceding aspects comprising a filler selected from the group consisting of sugars, starches, modified starches, sugar alcohols, cellulose derivatives, inorganic substances and mixtures thereof.

In a ninth aspect, the present invention relates to a tablet according to any of the preceding aspects comprising a binder selected from the group consisting of celluloses, cellulose derivates, starches, modified starches, polyethyleneglycols, polyvinylpyrrolidones, polyvinyl acetates, polyvinyl alcohols and mixtures thereof.

In a tenth aspect, the present invention relates to a tablet according to any of the preceding aspects comprising a disintegrant selected from the group consisting of sodium starch glycolate, crospovidone, crosscarmellose, sodium carboxymethylcellulose, dried corn starch and mixtures thereof.

In an eleventh aspect, the present invention relates to a tablet according to any of the preceding aspects comprising a glidant selected from the group consisting of colloidal silicon dioxide, light anhydrous silicic acid and mixtures thereof.

In a twelfth aspect, the present invention relates to a tablet according to any of the preceding aspects comprising a lubricant selected from the group consisting of stearic acid, magnesium stearate, sodium stearylfumarate, talcum, glycerol tribehenate, polyethylene glycol and mixtures thereof.

In a thirteenth aspect, the present invention relates to a tablet according to any of the preceding aspects comprising a filler selected from the group consisting of lactose, mannitol, microcrystalline cellulose, pregelatinized starch, calcium phosphate, dibasic calcium phosphate and mixtures thereof.

In a fourteenth aspect, the present invention relates to a tablet according to any of the preceding aspects comprising lactose, preferably lactose monohydrate as a filler, wherein the lactose has a $D_{90}$ of 100 to 600 µm, preferably of 150 to 500 µm.

In a fifteenth aspect, the present invention relates to a tablet according to any of the preceding aspects comprising:

| | |
|---|---|
| Afatinib Dimaleate | 1 to 50% w/w |
| Lactose Monohydrate | 20 to 90% w/w |
| Microcrystalline cellulose | 1 to 40% w/w |
| Crospovidone | 0.5 to 15% w/w |
| Colloidal silicon dioxide | 0.1 to 5% w/w |
| Magnesium stearate | 0.5 to 10% w/w |
| Hydroxymethyl propylcellulose based Coating | 2 to 5% w/w |

In a sixteenth aspect, the present invention relates to a process for manufacturing a tablet according to any of the preceding claims comprising:
i) Providing Afatinib dimaleate form L or a blend of Afatinib dimaleate form L and one or more pharmaceutically acceptable excipients;
ii) Mixing Afatinib or a pharmaceutically acceptable salt thereof or the blend obtained in step i) with at least one lubricant and
iii) Compressing the lubricated blend obtained step ii) to form a tablet.

In a seventeenth aspect, the present invention relates to a tablet according to any of the aspects 1 to 16 for use in the treatment of cancer.

In an eighteenth aspect, the present invention relates to a tablet comprising Afatinib dimaleate form L and lactose, preferably lactose monohyrate; wherein tablet is obtained by direct compression.

In a nineteenth aspect, the present invention relates to a tablet comprising Afatinib or a pharmaceutically acceptable salt thereof, wherein Afatinib is present as crystalline Afatinib dimaleate form L and tablet is obtained by direct compression.

In a twentieth aspect, the present invention relates to a tablet comprising Afatinib or a pharmaceutically acceptable salt thereof obtained by direct compression, wherein Afatinib is present as crystalline Afatinib dimaleate form L and preferably polymorphic form is retained during compression/does not change during compression as depicted in the FIGURE.

Embodiments

1. Tablet comprising Afatinib or a pharmaceutically acceptable salt thereof, wherein the tablet is obtained by direct compression.
2. Tablet according to embodiment 1, comprising Afatinib dimaleate. 3. Tablet according to embodiment 1 or 2, comprising crystalline Afatinib dimaleate.
4. Tablet according to any of the preceding embodiments comprising crystalline
Afatinib dimaleate form A, form F, form G, form H, form I, form J, form K, form L or form M, preferably form L.
5. Tablet according to embodiment 1 comprising crystalline Afatinib, preferably crystalline Afatinib form E or form F.
6. Tablet according to any of the preceding embodiments, further comprising one or more pharmaceutically acceptable excipients.
7. Tablet according to any of the preceding embodiments comprising at least one filler, at least one binder, at least one disintegrant, at least one glidant and at least one lubricant.
8. Tablet according to any of the preceding embodiments comprising a filler selected from the group consisting of sugars, starches, modified starches, sugar alcohols, cellulose derivatives, inorganic substances and mixtures thereof.
9. Tablet according to any of the preceding embodiments comprising a binder selected from the group consisting of celluloses, cellulose derivates, starches, modified starches, polyethyleneglycols, polyvinylpyrrolidones, polyvinylacetates, polyvinyl alcohols and mixtures thereof.
10. Tablet according to any of the preceding embodiments comprising a disintegrant selected from the group consisting of sodium starch glycolate, crospovidone, crosscarmellose, sodium carboxymethylcellulose, dried corn starch and mixtures thereof
11. Tablet according to any of the preceding embodiments comprising a glidant selected from the group consisting of colloidal silicon dioxide, light anhydrous silicic acid and mixtures thereof
12. Tablet according to any of the preceding embodiments comprising a lubricant selected from the group consisting of stearic acid, magnesium stearate, sodium stearylfumarate, talcum, glycerol tribehenate, polyethylene glycol and mixtures thereof
13. Tablet according to any of the preceding embodiments comprising a filler selected from the group consisting of lactose, mannitol, microcrystalline cellulose, pregelatinized starch, calcium phosphate, dibasic calcium phosphate and mixtures thereof
14. Tablet according to any of the preceding embodiments comprising lactose, preferably lactose monohydrate as a filler, wherein the lactose preferably has a $D_{90}$ of 100 to 600 µm, preferably of 150 to 500 µm.

15. Tablet according to any of the preceding embodiments comprising:

| | |
|---|---|
| Afatinib Dimaleate | 1 to 50% w/w |
| Lactose Monohydrate | 20 to 90% w/w |
| Microcrystalline cellulose | 1 to 40% w/w |
| Crospovidone | 0.5 to 15% w/w |
| Colloidal silicon dioxide | 0.1 to 5% w/w |
| Magnesium stearate | 0.5 to 10% w/w |
| Hydroxypropyl methylcellulose based coating | 2 to 5% w/w |

16. Process for manufacturing a tablet according to any of the preceding claims comprising:
   iv) Providing Afatinib dimaleate form L or a blend of Afatinib dimaleate form L and one or more pharmaceutically acceptable excipients;
   v) Mixing Afatinib or a pharmaceutically acceptable salt thereof or the blend obtained in step i) with at least one lubricant and
   vi) Compressing the lubricated blend obtained step ii) to form a tablet.
17. Tablet according to any of the embodiments 1 to 16 for use in the treatment of cancer.
18. Method of treating cancer comprising administering a tablet according to any of the embodiments 1 to 16 to a subject in need thereof.
19. Method according to embodiment 18, wherein the tablet comprises a therapeutically effective amount of Afatinib.
20. A process for manufacturing a tablet according to any of embodiments 1 to 19 comprising:
   i) Mixing Afatinib or a pharmaceutically acceptable salt thereof with a filler, a binder, a disintegrant and a glidant,
   ii) Mixing the blend obtained in step i) with a lubricant and,
   iii) Compressing the lubricated blend obtained step ii) to form a tablet.
21. Process for manufacturing a tablet according to any of the embodiments 1 to 20 comprising:
   i) Mixing Afatinib or a pharmaceutically acceptable salt thereof with lactose monohydrate having a $D_{90}$ of 100 to 600 µm, preferably of 150 to 500 µm, microcrystalline cellulose, crospovidone and colloidal silicon dioxide,
   ii) Mixing the blend obtained in step i) with magnesium stearate and,
   iii) Compressing the lubricated blend obtained step ii) to form a tablet,
   iv) Optionally coating the compressed tablets, preferably with a hydroxypropyl methylcellulose based coating.
22. Tablet according to any of embodiments 1 to 17 comprising a coating, preferably a hydroxypropyl methylcellulose based coating.
23. Tablet comprising Afatinib dimaleate form L and lactose, preferably lactose monohyrate; wherein tablet is obtained by direct compression.
24. Tablet comprising Afatinib or a pharmaceutically acceptable salt thereof, wherein Afatinib is present as crystalline Afatinib dimaleate form L and tablet is obtained by direct compression.
25. Tablet comprising Afatinib or a pharmaceutically acceptable salt thereof obtained by direct compression, wherein Afatinib is present as crystalline Afatinib dimaleate form L and preferably the polymorphic form is retained during compression/does not change during compression as depicted in the FIGURE.

EXAMPLES

Examples 1 to 11 relate to the preparation of Afatinib and various polymorphs as described in our copending application 1769/DEL/2015 filed on Jun. 12, 2015.

Example-1: Preparation of Afatinib

A mixture of (E)-4-(dimethylamino) but-2-enoic acid hydrochloride (44.1 g) and dimethyl acetamide (350 ml) was cooled at −15 to −20° C. To this solution 28.6 g of thionyl chloride was added dropwise and stirred at −15 to −20° C. for 3-4 h (designated as solution-1). In a separate container $N^4$-(3-chloro-4-fluorophenyl)-7-[(3S)-tetrahydrofuran-3-yloxy]quinazoline-4,6-diamine (50 g) was dissolved in 150 ml dimethylacetamide and added to the solution-1 at −20 to −25° C. The reaction mixture was stirred for 1-2 h. To this reaction mass charged water (100 ml) followed by stirring for 10 min(designated as solution-2). A solution of sodium carbonate prepared separately by dissolving 125 g potassium carbonate in 1900 ml of purified water (designated as solution-3). The solution-2 was added into the solution-3 and solid obtained stirred for 2-3 hr. The solid was filtered and suspended in water and pH adjusted to 2-5 using hydrochloric acid solution. Ethyl acetate (500 ml) added and reaction mass stirred for 1-1.5 h. Ethyl acetate layer separated and discarded. The aqueous layer was neutralized with potassium carbonate and pH was maintained at around 8-9. The solid obtained stirred for further 2 h and filtered followed by drying to get 48 g of the Afatinib.

Example-2: Preparation of Crystalline Form E Afatinib

A solution of Afatinib (55.0 g) in acetone (165 ml) was stirred for 20-30 min at room temperature. Methyl tertiary butyl ether (165 ml) was added and the reaction mass was cooled to −10 to −15° C. The reaction mass was stirred for 1-2 h at −10 to −15° C. The solid thus obtained was filtered and washed with chilled methyl tertiary butyl ether (55 ml). The solid was suck dried for 1-2 h followed by drying under reduced pressure NLT (700 mmHg) for 10-12 h. 48 g of crystalline form E of Afatinib was obtained.
Water Content: 2.26%

Example-3: Preparation of Crystalline Form F Afatinib

To a solution of Afatinib (50.0 g) in dichloromethane (350 ml) methyl tertiary butyl ether (350 ml) was added slowly over a period of 30 min. The reaction mass was stirred for 1 h at 20-30° C. followed by cooling at 0-5° C. The reaction mass was continue to stirred for 1 h at 0-5° C. and solid thus formed was filtered and washed with chilled methyl tertiarybutyl ether 100 ml). The solid was suck dried for 1 h at room temperature and further at 50° C. under reduced pressure NLT (700 mmHg) for 12 h. 48 g form F of Afatinib was obtained.
Water Content: 3.71%

Example 4: Preparation of Crystalline Form F of Afatinib Dimaleate

A mixture of ethyl acetate (60 ml) and Afatinib (3.0 g) was stirred at 20-30° C. to get a clear solution. A solution of maleic acid [prepared by dissolving 1.54 g of maleic acid in 45 ml of ethyl acetate] was added to the above solution in 10-15 min at 20-30° C. The reaction mass was stirred for 2 h at 20-30° C. The solid thus formed was filtered, washed with ethyl acetate (15 ml) and dried at 40° C. for 10 h. 4 g of crystalline form F of Afatinib dimaleate was obtained.

Water Content: 4.54% (w/w)

Example-5: Preparation of Crystalline Form G of Afatinib Dimaleate

A solution of Afatinib (3.0 g) in dimethyl formamide (15 ml) was stirred at 20-30° C. Another solution was prepared by dissolving maleic acid (1.50 g) in dimethyl formamide (6.0 ml) and added to the previous solution. The reaction mixture was stirred for 15 min and then cooled to 0-10° C. Methyl tertiary butyl ether (90 ml) was added to resulting solution in 15 min and stirred for 2 h at 0-10° C. The resulting solid was filtered, washed with methyl tertiary butyl ether (30 ml) and suck dried for 10 min under vacuum at 40° C. for 10 h. 4 g of crystalline form G of Afatinib dimaleate was obtained.

Water Content: 0.46% (w/w)

Example-6: Preparation of Crystalline Form H of Afatinib Dimaleate

A solution of Afatinib (3.0 g) in acetonitrile (60 ml) was stirred at 20-30° C. for 10 min. A separately prepared solution of maleic Acid (prepared by dissolving maleic acid (1.50 g) in 45 ml of acetonitrile) was added and the reaction mass was stirred overnight. The solid thus obtained was filtered, washed with acetonitrile (30 ml), suck dried for 10 min and then dried under vacuum at 40° C. for 10 h. 3 g of crystalline form H of Afatinib dimaleate was obtained.

Water Content: 1.22% (w/w)

Example-7: Preparation of Crystalline Form I of Afatinib Dimaleate

A solution of Afatinib (2.0 g) in dimethylformamide (4 ml) was stirred at 20-30° C. for 5 min. A separately prepared solution of maleic acid (prepared by dissolving 1.0 g of maleic acid in 2 ml of dimethylformamide) was added to above solution in 10 min. Thereafter, dichloromethane (60 ml) was added in 20 min period and mixture was stirred for 2 h. Product thus obtained was filtered and washed with dichloromethane (20 ml). After suck drying for 30 min, the solid was again suspended in dichloromethane (40 ml) and stirred for 1 h. The product was filtered, washed with dichloromethane (20 ml) and suck dried for 30 min. Resulting solid was further dried under vacuum at 50-60° C. for 12 h. 2.2 g of crystalline form I of Afatinib dimaleate was obtained.

Water Content: 2.85%

Example-8: Preparation of Crystalline Form J of Afatinib Dimaleate

A solution of Afatinib (5.0 g) in acetone (125 ml) was stirred at 20-30° C. for 10 min. methyl tertiary butyl ether (100 ml) was charged in 10 min. Maleic acid solution [Prepared by dissolving maleic acid (2.5 g) in acetone (25 ml)] was added in the reaction mass. The reaction mass was stirred for 2 h at 20-30° C. The solid thus formed was filtered and washed with methyl tertiary butyl ether (50 ml). The product was suck dried for 15 min. and under vacuum at 40° C. for 12 h. 6.5 g of crystalline form J of Afatinib dimaleate was obtained.

Water Content: 1.46%

Example-9: Preparation of Crystalline Form K of Afatinib Dimaleate

A solution of Afatinib (5.0 g) in ethyl acetate (100 ml) was stirred at 20-30° C. for 10-15 min. Methyl tertiary butyl ether (100 ml) was added and the solution was stirred for 15 min at 25-30° C. A solution of maleic acid [prepared by dissolving maleic acid (2.5 g) in ethyl acetate (75 ml)] was added in the reaction mixture and stirred for 24 h at 25-30° C. The solid thus formed was filtered and washed with methyl tertiary butyl ether (40 ml) followed by suck drying for 15 min. The product was finally dried under vacuum at 40° C. for 24 h. 6.3 g of crystalline form K of Afatinib dimaleate was obtained.

Water Content: 2.27%

Example-10: Preparation of Crystalline Form L of Afatinib Dimaleate

A solution of Afatinib (9.0 gm) in acetonitrile (180 ml) was stirred at 20-30° C. for 10 min. A solution of maleic Acid [prepared by dissolving maleic acid (4.5 g) in acetonitrile (180 ml)] was added to the solution slowly at 20-30° C. in 20 min. The reaction mass was stirred for 2 h followed by filtration. The solid thus obtained was washed with acetonitrile (18.0 ml) and suck dried for 15 min. The solid was further dried under vacuum for 6.0 hr at 25° C. The dried material (7.0 g) was charged in a flask followed by addition of ethyl acetate (70 ml) and stirred for 2 h at 20-30° C. The solid was filtered and washed with ethyl acetate (20 ml) and suck dried for 15 min. The product finally dried in oven under vacuum at 45° C. for 15-16 h. 8.4 g of crystalline form L of Afatinib dimaleate was obtained Water Content: 1.61%

Example-11: Preparation of Crystalline Form M of Afatinib Dimaleate

A solution of Afatinib (15.0 g) in acetonitrile (300 ml) was stirred at room temperature for 30 min. The clear solution was filtered through 5 micron filter paper. The filtrate was charged in the flask and ⅔ of maleic acid solution [prepared by dissolving maleic acid (9.1 g) in dimethylsulfoxide (10 ml) and acetonitrile (10 ml] was added drop wise. The reaction mass was stirred for 15-20 min followed by addition of rest of the maleic acid solution. After complete addition the reaction mass was stirred for 1-2 h at 20-35° C. The solid thus formed was filtered and washed with acetonitrile (15 ml) and suck dried for 10-15 min. The product thus obtained was charged in the reactor and acetonitrilec (150 ml) was added. The reaction mas was stirred for 15 min and then filtered under nitrogen. The product was washed with acetonitrile (15 ml×2). The product was suck dried for 1-2 h and then dried under vacuum (NLT 700 mmHg) for 5-6 h. The resulting product was charged in a flask and ethyl acetate (600 ml) was added and reaction mass was stirred for 90 min. The solid thus formed was filtered, washed with ethyl acetate (150 ml) and suck dried for 20-30 min. and finally under vacuum (NLT 700 mmHg) at 45° C. for 20-22 h. 18.8 g of crystalline form M of Afatinib dimaleate was obtained Water Content: 2.54%

Examples 12 and 13 are Directed Towards the Tablets Comprising Afatinib Dimaleate of the Present Invention Examples 12 & 13

Directly compressed tablets comprising Afatinib dimaleate using ingredients as listed in table 1.

TABLE 1

| | | Example 12 | | | Example 13 | | |
|---|---|---|---|---|---|---|---|
| | | Batch A | Batch B | Batch C | Batch A | Batch B | Batch C |
| S. N | Name of the | 20 mg (mg/tab) | 30 mg (mg/tab) | 40 mg (mg/tab) | 20 mg (mg/tab) | 30 mg (mg/tab) | 40 mg (mg/tab) |
| 1. | Afatinib Dimaleate (Form L) | 29.65 | 44.34 | 59.12 | — | — | — |
| | Afatinib Dimaleate (Form A) | — | — | — | 29.65 | 44.34 | 59.12 |
| 2. | Lactose Monohydrate | 123.86 | 185.79 | 247.72 | 123.86 | 185.79 | 247.72 |
| 3. | Microcrystalline cellulose | 18.48 | 27.72 | 36.96 | 18.48 | 27.72 | 36.96 |
| 4. | Crospovidone | 3.60 | 5.40 | 7.20 | 3.60 | 5.40 | 7.20 |
| 5. | Colloidal silicon dioxide | 0.90 | 1.35 | 1.80 | 0.90 | 1.35 | 1.80 |
| 6. | Magnesium stearate | 3.60 | 5.40 | 7.20 | 3.60 | 5.40 | 7.20 |
| | Total (core tablet) | 180.09 | 270.00 | 360.00 | 180.09 | 270.00 | 360.00 |
| 7. | Coating solution | 5.40 | 8.10 | 10.80 | — | — | — |
| | containing Hydroxypropyl methylcellulose, titanium dioxide, propylene ethylene glycol, talc, polysorbate 80 and color pigments | | | | | | |
| 8. | Total (coated tablet) | 185.49 | 278.10 | 370.80 | 180.09 | 270.00 | 360.00 |

Brief Manufacturing Procedure:

The exemplary formulations were prepared by direct compression and aqueous film-coating process:
1. Afatinib dimaleate, lactose monohydrate, microcrystalline cellulose, crospovidone and colloidal silicon dioxide were mixed and sifted with sieve no. 25 to produce a homogenous mix.
2. The blend obtained in step 1 was lubricated using magnesium stearate.
3. The lubricated blend was compressed into tablets.
4. The tablets were optionally coated with coating solution containing hydroxypropyl methyl cellulose, titanium dioxide, propylene ethylene glycol, talc, polysorbate 80 and color pigments and using pan spray coating machine at product temperature 35 to 45° C.
5. The tablets were packed in a suitable packaging material.

The uncoated tablets of examples 12 & 13 of the present invention were subjected to the evaluation of various parameters as described below:

Tablet Evaluation:

Tablets comprising two different polymorphs prepared by direct compression were subjected to tablet evaluation for the following important parameters:

All values were measured using standard procedures.

Tablets according to example 12 batch C and example 13 batch C were evaluated with respect to various parameters necessary for maintaining tablet integrity and rate of release required for standard tablets and results obtained are compiled in table 2:

TABLE 2

| Parameter | Example 12. batch C | Example 13. batch C |
|---|---|---|
| Lamination | Not observed | Not observed |
| Capping | Not observed | Not observed |
| Sticking | Not observed | Not observed |

TABLE 2-continued

| Parameter | Example 12. batch C | Example 13. batch C |
|---|---|---|
| Disintegration time (mins) | 3-6 | 2-6 |
| Weight (mg) | 350-370 | 350-370 |
| Assay (%) | 99.7 | 102.5 |
| Hardness (kp) | 8 to 12 | 8 to 12 |

Dissolution Studies:

Dissolution media-Mcilvaine Buffer pH 4.0, volume 900 ml, temperature 37.0° C.

Apparatus—USP II at 75 rpm,

Table 3 depicts that the results of Dissolution of tablets of Afatinib dimaleate obtained via direct compression comply with the USP limits for immediate release tablets.

TABLE 3

| Time (min) | Percentage drug release with Ex. 12 (batch C) | Percentage drug release with Ex. 13 (batch C) |
|---|---|---|
| 10 | 69 | 102 |
| 15 | 95 | 103 |
| 20 | 102 | 103 |
| 30 | 101 | 103 |
| 45 | 100 | 103 |

Content uniformity of tablets were found to be adequate using direct compression, results are summarized in table 4:

TABLE 4

| Content uniformity for different tablets | Percentage of label claim for Ex. 12 (batch C) | Percentage of label claim for Ex. 13 (batch C) |
|---|---|---|
| Tablet 1 | 98.5 | 101.9 |
| Tablet 2 | 100.5 | 101.5 |
| Tablet 3 | 99.9 | 104.1 |
| Tablet 4 | 99.9 | 104.1 |
| Tablet 5 | 97.8 | 101.6 |
| Tablet 6 | 101.5 | 102.3 |
| Tablet 7 | 100.5 | 101.8 |
| Tablet 8 | 99.4 | 103.8 |
| Tablet 9 | 100.0 | 103.0 |
| Tablet 10 | 100.1 | 102.5 |
| Average | 99.8 | 102.7 |
| Relative Standard Deviation (RSD) | 1.047 | 1.00 |

The results presented in table 4 show that the tablets according to the present invention obtained by direct compression are comparable to Afatinib tablets obtained by dry compaction with respect to uniformity of content (compare table 3 of U.S. Pat. No. 8,545,884, Col. 16).

We claim:

1. A tablet comprising Afatinib dimaleate form L, wherein the tablet is obtained by direct compression, and the Afatinib dimaleate form L is characterized by (a) an X-ray powder diffractogram having peaks at 5.2, 10.3, 11.1, 15.5, 18.1±0.2 degrees two-theta, or (b) endothermic peaks at 125 and 171±2° C. as measured by differential scanning calorimetry (DSC).

2. The tablet according to claim 1, further comprising one or more pharmaceutically acceptable excipients.

3. The tablet according to claim 1, further comprising at least one filler, at least one binder, at least one disintegrant, at least one glidant and at least one lubricant.

4. The tablet according to claim 1, further comprising a filler selected from sugars, starches, modified starches, sugar alcohols, cellulose derivatives, inorganic substances, and mixtures thereof.

5. The tablet according to claim 1, further comprising a binder selected from celluloses, cellulose derivates, starch, modified starches, polyethyleneglycols, polyvinylpyrrolidones, polyvinylacetates, polyvinylalcohols, and mixtures thereof.

6. The tablet according to claim 1, further comprising a disintegrant selected from sodium starch glycolate, crospovidone, crosscarmellose, sodium carboxymethylcellulose, dried corn starch, and mixtures thereof.

7. The tablet according to claim 1, further comprising a glidant selected from colloidal silicon dioxide, light anhydrous silicic acid, and mixtures thereof.

8. The tablet according to claim 1, further comprising a lubricant selected from stearic acid, magnesium stearate, sodium stearylfumarate, talcum, glycerol tribehenate, polyethylene glycol, and mixtures thereof.

9. The tablet according to claim 1, further comprising a filler selected from lactose, mannitol, microcrystalline cellulose, pre-gelatinized starch, calcium phosphate, dibasic calcium phosphate, and mixtures thereof.

10. The tablet according to claim 1, further comprising lactose, wherein the lactose has a $D_{90}$ of 100 to 600 μm.

11. The tablet according to claim 1, comprising: (1) a core comprising 1-50% w/w Afatinib dimaleate form L, 20-90% w/w lactose monohydrate, 1-40% w/w microcrystalline cellulose, 0.5-15% w/w crospovidone, 0.1-5% w/w colloidal silicon dioxide, and 0.5-10% w/w magnesium stearate; and (2) a coating in an amount of 2-5 wt. % based on the core weight, wherein the coating comprises hydroxypropyl methylcellulose.

12. A process for manufacturing a tablet according to claim 1, comprising:
mixing Afatinib dimaleate form L or a blend of Afatinib dimaleate form L and one or more pharmaceutically acceptable excipients with at least one lubricant; and
compressing the lubricated blend to form a tablet.

13. A method of treating cancer, the method comprising administering the tablet of claim 1 to a subject in need thereof.

14. The tablet according to claim 1, comprising lactose.

15. The tablet according to claim 1, wherein the Afatinib dimaleate form L is characterized by an X-ray powder diffractogram having peaks at 5.2, 10.3, 11.1, 15.5, 18.1±0.2 degrees two-theta.

16. The tablet according to claim 1, wherein the Afatinib dimaleate form L is characterized by endothermic peaks at 125 and 171±2° C. as measured by DSC.

17. The tablet according to claim 15, wherein the Afatinib dimaleate form L is characterized by endothermic peaks at 125 and 171±2° C. as measured by DSC.

18. The tablet according to claim 15, comprising: (1) a core comprising 1-50% w/w Afatinib dimaleate form L, 20-90% w/w lactose monohydrate, 1-40% w/w microcrystalline cellulose, 0.5-15% w/w crospovidone, 0.1-5% w/w colloidal silicon dioxide, and 0.5-10% w/w magnesium stearate; and (2) a coating in an amount of 2-5 wt. % based on the core weight, wherein the coating comprises hydroxypropyl methylcellulose.

19. The tablet according to claim 16, comprising: (1) a core comprising 1-50% w/w Afatinib dimaleate form L, 20-90% w/w lactose monohydrate, 1-40% w/w microcrystalline cellulose, 0.5-15% w/w crospovidone, 0.1-5% w/w colloidal silicon dioxide, and 0.5-10% w/w magnesium stearate; and (2) a hydroxypropyl methylcellulose based coating in an amount of 2-5 wt. % based on the core weight.

20. The tablet according to claim 17, comprising: (1) a core comprising 1-50% w/w Afatinib dimaleate form L, 20-90% w/w lactose monohydrate, 1-40% w/w microcrystalline cellulose, 0.5-15% w/w crospovidone, 0.1-5% w/w colloidal silicon dioxide, and 0.5-10% w/w magnesium stearate; and (2) a coating in an amount of 2-5 wt. % based on the core weight, wherein the coating comprises hydroxypropyl methylcellulose.

* * * * *